United States Patent
Hampe et al.

(10) Patent No.: US 10,195,120 B2
(45) Date of Patent: *Feb. 5, 2019

(54) CURABLE DENTAL RETRACTION COMPOSITION, METHOD OF PRODUCTION AND USE THEREOF

(75) Inventors: Ruediger Hampe, Wörthsee (DE);
Thomas Klettke, Diessen (DE);
Andreas R. Maurer, Langenneufnach (DE); Christoph Schulte, Windach (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/677,831

(22) PCT Filed: Sep. 9, 2008

(86) PCT No.: PCT/US2008/075687
§ 371 (c)(1),
(2), (4) Date: Mar. 12, 2010

(87) PCT Pub. No.: WO2009/035961
PCT Pub. Date: Mar. 19, 2009

(65) Prior Publication Data
US 2010/0261143 A1 Oct. 14, 2010

(30) Foreign Application Priority Data

Sep. 14, 2007 (EP) ..................................... 07116451

(51) Int. Cl.
*A61K 6/00* (2006.01)
*C07H 3/06* (2006.01)
(Continued)

(52) U.S. Cl.
CPC .......... *A61K 6/0011* (2013.01); *A61C 9/0033* (2013.01); *A61K 6/0047* (2013.01);
(Continued)

(58) Field of Classification Search
CPC ....... C04B 14/02; C04B 28/344; C04B 22/06; C04B 28/346; C04B 14/303
(Continued)

(56) References Cited

U.S. PATENT DOCUMENTS 2,345,255 A * 3/1944 Gross ........................ A61K 6/10
106/217.9
3,620,778 A * 11/1971 Morrell ........................ 523/109
(Continued)

FOREIGN PATENT DOCUMENTS

DE  3737552   5/1989
EP  1886659   2/2008
(Continued)

OTHER PUBLICATIONS

Hugo Lemes Carlol et al; "Analysis of filler particle levels and sizes in dental alginates";Mat. Res. vol. 13 No. 2 São Carlos Apr./Jun. 2010.*

(Continued)

*Primary Examiner* — Shuangyi Abu Ali
(74) *Attorney, Agent, or Firm* — Eric Silverman

(57) ABSTRACT

The invention relates to a curable dental retraction composition comprising alginate and a solvent, with the proviso that essentially no crosslinker in an amount effective to start setting of the curable dental retraction composition is present. The invention also relates to a container containing said composition and to a kit comprising two parts, wherein the first part comprises the curable dental retraction composition
(Continued)

of the present invention and the second part comprises a crosslinker being able to start setting of the dental retraction composition.

22 Claims, 2 Drawing Sheets

(51) Int. Cl.
    *A61C 19/06*     (2006.01)
    *A61K 6/097*     (2006.01)
    *A61C 9/00*     (2006.01)

(52) U.S. Cl.
    CPC .......... *A61K 6/0088* (2013.01); *A61K 6/0091* (2013.01); *A61K 6/0094* (2013.01); *A61K 6/097* (2013.01)

(58) Field of Classification Search
    USPC ........................................................ 106/35
    See application file for complete search history.

(56) References Cited

U.S. PATENT DOCUMENTS

| | | | |
|---|---|---|---|
| 4,232,638 A | | 11/1980 | Day |
| 4,260,597 A | | 4/1981 | Porteous |
| 4,321,038 A | | 3/1982 | Porteous |
| 4,381,947 A | * | 5/1983 | Pellico ............... 106/38.51 |
| 4,465,462 A | | 8/1984 | Ticknor |
| 4,522,593 A | | 6/1985 | Fischer |
| 4,597,960 A | | 7/1986 | Cohen |
| 4,617,950 A | | 10/1986 | Porteous |
| 4,854,867 A | | 8/1989 | Meinershagen |
| 4,871,311 A | | 10/1989 | Hagne |
| 4,892,482 A | | 1/1990 | Lococo |
| 4,907,602 A | * | 3/1990 | Sanders ............... 607/72 |
| 4,959,220 A | * | 9/1990 | Yamamoto ....... A61K 6/10 424/490 |
| 5,358,403 A | | 10/1994 | Groth |
| 5,362,495 A | | 11/1994 | Lesage |
| 5,480,303 A | | 1/1996 | Groth |
| 5,540,588 A | | 6/1996 | Earle |
| 5,635,162 A | | 6/1997 | Fischer |
| 5,785,955 A | | 7/1998 | Fischer |
| 5,865,803 A | | 2/1999 | Major |
| 5,893,714 A | | 4/1999 | Arnold |
| 5,899,694 A | | 5/1999 | Summer |
| 5,927,562 A | | 7/1999 | Hammen |
| 6,116,905 A | | 9/2000 | Hoos |
| 6,375,461 B1 | | 4/2002 | Jensen |
| 6,383,279 B1 | | 5/2002 | Eckhardt |
| 6,568,398 B2 | | 5/2003 | Cohen |
| 6,575,749 B1 | | 6/2003 | Greenwald |
| 8,142,562 B2 | * | 3/2012 | Klettke ............ A61K 6/0011 106/35 |
| 2002/0156149 A1 | | 10/2002 | Schaub |
| 2004/0106086 A1 | | 6/2004 | Dragan |
| 2005/0008583 A1 | | 1/2005 | White |
| 2005/0069833 A1 | | 3/2005 | Kollefrath |
| 2005/0250871 A1 | | 11/2005 | Bublewitz |
| 2005/0260543 A1 | | 11/2005 | Dragan |
| 2005/0287494 A1 | | 12/2005 | Yang |
| 2006/0159823 A1 | * | 7/2006 | Melvik et al. ............ 426/575 |
| 2007/0172789 A1 | | 7/2007 | Muller |

FOREIGN PATENT DOCUMENTS

| | | | |
|---|---|---|---|
| EP | 1707178 | | 7/2011 |
| JP | 10-139617 | * | 5/1998 |
| JP | 2006/056833 | | 3/2006 |
| WO | WO 1996/14453 | | 5/1996 |
| WO | WO 2004/082510 | | 9/2004 |
| WO | WO 2005/122945 | | 12/2005 |
| WO | WO 2006/002939 | | 1/2006 |
| WO | WO 2006/057535 | | 6/2006 |
| WO | WO 2006/089857 | | 8/2006 |

OTHER PUBLICATIONS

Draget, "Alginates", Chapter 22, Handbook of Hydrocolloids, Edited by Phillips and Williams, Woodhead Publishing, 2000, pp. 379-395.
ISO 37.
Written Opinion of the ISA for International Application No. PCT/US2008/075687, pp. 6.
International Search Report from PCT/US2008/075687, pp. 3.
European Search Report from 07116451.1 1219, pp. 8.

* cited by examiner

CURABLE DENTAL RETRACTION COMPOSITION, METHOD OF PRODUCTION AND USE THEREOF

CROSS REFERENCE TO RELATED APPLICATIONS

This application is a national stage filing under 35 U.S.C. § 371 of PCT/US2008/075687, filed Sep. 9, 2008, which claims priority to EP Application No. 07116451.1, filed Sep. 14, 2007, the disclosure of which is incorporated by reference in its/their entirety herein.

FIELD OF THE INVENTION

The invention relates to a curable dental retraction composition, a method for production and the use thereof.

BACKGROUND ART

For retracting gingiva from a prepared tooth a cord can be used. In this respect, a retraction cord is packed between gingival tissue and the margin of the prepared tooth (this region is also often called sulcus) using an appropriate dental instrument e.g. a Heinemann spatula. To obtain sufficient vertical and horizontal retraction of gingival tissue, it is often necessary to pack several lengths of retraction cord into the sulcus in order to be able to make a detailed dental impression.

A description of the background in regard to retraction cords can be found e.g. in U.S. Pat. No. 4,522,593.

U.S. Pat. No. 4,871,311 describes a retraction method using a retraction cord made at least in part of a swelling material.

Generally, dental retraction cords are sometimes difficult to place into the gingival sulcus. The procedure can also be time consuming. It can also be cumbersome to remove the retraction cord prior to taking the impression. Coagulated blood may adhere to the cord and removing it may open the wound again which results in bleeding.

For a more convenient placement retraction pastes have been suggested.

Non-hardening retraction pastes containing either an anti-evaporating component or fibrillated fibers are described in e.g. US 2005/0008583 and US2005/00287494.

U.S. Pat. No. 5,362,495 refers to a method for widening the gingival sulcus without bleeding or oozing, comprising inserting within the gingival sulcus a material in the form of a biocompatible paste which is injectable for external use and having a plastic viscosity measured at 20° C. between about 13,000 and 30,000 Pa*s, wherein said material consisting of a material selected from the group of white clay, seaweed meal and mixtures thereof.

A similar approach is described in JP 2006056833. The paste consists of an astringent and filler containing clay mineral, torque, mica, kaolin and/or montmorillonite.

A commercially available product to be used for retraction is sold under the name Expasyl™. However it is reviewed, that Expasyl™ is only effective under specific, limited conditions when the sulcus is flexible and of sufficient depth. The paste's thickness makes it difficult for some evaluators to express it into the sulcus. Moreover, according to the instruction of use, the viscosity of the composition might change when fluids like water, saliva or blood are absorbed. However, a reduction in viscosity is sometimes undesirable since having high consistency could in certain circumstances be a pre-requisite for applying force onto the gingiva for sufficient retraction.

Generally, removing non-hardening pastes completely out of the sulcus before taking the impression can be very time consuming and cumbersome. Usually, the paste is rinsed off using water-spray. However, sometimes paste residues are located deep in the sulcus and are thus difficult to remove. These residues might prevent the impression material from flowing into the sulcus area and may negatively influence the setting of the impression material which is subsequently applied. Moreover, after rinsing off the paste with water an additional drying step might be required before the impression can be taken. These removing and drying steps could cause bleeding of the tissue and might make an impression taking step more complicated.

Hardening materials are sometimes easier to remove. However, they are not very hydrophilic. This might cause problems with regard to flowability of the material into the gingival sulcus.

US 2004/0106086 describes an impression material which can be used for retraction of gingival tissue.

US 2005/0260543 describes a method or retracting gum tissue comprising the steps of placing an initially flow able material around a tooth, covering the tooth and flow able material with a dam made of a porous material, applying pressure to the dam and removing the dam with the set material.

US 2005/0069838 discloses a dental kit and method for retraction sulcus using an expanding silicone compound or mixture of different silicone compounds. However, silicone compounds are of inorganic and hydrophobic nature, thus having limited biocompatibility with oral tissue and disadvantages in flowing to moist tissue and tooth surfaces and moist areas like the gingival sulcus.

DE 37 37 552 A1 suggests to use alginates, hydrocolloids or silicone for dental retraction. No hints as to the nature of the materials to be used for the retraction procedure are given. It is only mentioned that some kind of reaction should take place (expansion by chemical reaction and/or physical swelling of the material) and that the material can be incorporated into a dental impression material selected from alginate, hydrocolloids and silicones, materials which cure after application.

Impression materials based on alginates are usually delivered in a powdery form which can form an irreversible hydrocolloide in the presence of water. The powder typically contains potassium or sodium alginic acid, filler(s), retarder(s) and additives. The pastes are made either by hand-mixing the powder and water or by using special mixing devices. Dental alginate impression materials usually have high filler content (generally above about 60 wt.-% with respect to the whole composition in dry form, that is, before water is added). Despite of this high filler content the set alginate materials have limited tensile strength because of their gel-like consistency after cure and thus are not suitable for use as a retraction material. Moreover, the setting time of this type of material is sometimes deemed to be too long for retraction procedure (e.g. above about 2 or 3 min).

Thus, there is still a need for an improved dental retraction composition. Ideally, a material is desired, which can be cured in the patients' mouth at a time convenient for the practitioner (e.g. on demand).

SUMMARY OF THE INVENTION

In one embodiment the present invention features a curable dental retraction composition comprising an alginate and a solvent (e.g. water), with the proviso that essentially no crosslinker in an amount effective to start setting of the curable dental retraction paste is present.

In another embodiment, the invention relates to a container having a front end and a rear end, a piston movable in the container and a nozzle for delivering the composition located in the container, the composition being the curable dental retraction composition as described in the present invention.

In a further embodiment, the invention is directed to a kit comprising two parts, wherein the first part comprises the curable dental retraction composition of the present invention and the second part comprises a crosslinker or crosslinker composition being able to start setting of the dental retraction composition.

The invention also relates to a process of curing a curable dental retraction composition, the process comprising the steps of providing the curable dental retraction composition and a crosslinker and bringing into contact the curable dental retraction composition and the crosslinker.

The invention also relates to a cured dental retraction composition obtainable according to the above described process.

The invention further features a method of using an alginate for the production of a curable retraction composition for retracting soft dental tissue/gingiva from hard dental tissue.

Moreover, the invention relates to a method of using the curable dental retraction composition, comprising the steps of applying or packing the curable dental retraction composition into the sulcus between soft and hard dental tissue and applying a crosslinker to at least the visible surface of the curable dental retraction composition.

It has been found that the dental retraction composition can easily be inserted in or onto the sulcus like e.g. a paste-like material. By applying to and/or packing the curable dental retraction composition into the sulcus, a mechanical retraction of the gingiva can be achieved.

In certain embodiments, the curable dental retraction has a viscosity being in a range which may allow an easy placement of the composition in the sulcus of a patient.

The paste-like composition can be changed into an elastic material for easier removal, e.g. by applying a crosslinker or crosslinker composition onto at least a part of the visible surface of the composition, if desired. Typically, after the setting process the paste can be removed in one or a few pieces, often without a further rinsing step. This might help in reducing the risk of opening the wounded tissue with a water beam when rinsing or with an air beam when drying prior to an impression taking step. Moreover, this may result in a safer and less time consuming procedure.

The cured retraction composition on the other hand may have a tensile strength in a range allowing an easy removal of the cured composition out of the sulcus.

Furthermore, the fact that the crosslinker used for setting the curable retraction composition is not present in the composition from the very beginning, enables the practitioner to apply the composition to the sulcus of a couple of teeth one after the other without time pressure and without running the risk that the composition already starts setting in the application device. The setting can be initiated afterwards or at any desired time—on demand—by applying the crosslinker in a separate step.

This is in contrast to the procedure described in DE 37 37 552, where the components of the composition to be applied are incorporated in an impression material containing all components needed for curing.

Thus, depending on the formulation chosen, the cured dental retraction composition of the invention can easily be removed from the sulcus, usually without using extensive water-spray.

Moreover, in certain embodiments the inventive curable dental retraction composition typically shows hydrophilic properties and thus can adhere well to hard and soft dental tissue (e.g. gingival).

In contrast to the state of the art retraction cords, certain embodiments of the dental retraction composition have a smooth surface. This may facilitate an easy removal out of the sulcus. The smooth surface may prevent sticking of the cured composition to coagulated blood which may be present in the sulcus. Sticking often may cause an undesired wound opening and bleeding upon removal of the retraction composition.

Certain embodiments of the inventive dental retraction composition are robust against fluids that might be present in the moist environment of the oral cavity, where the setting of the composition takes place (e.g., the retraction composition does not dissolve in saliva).

Due to the nature of the alginate component being present in the curable composition, the composition itself may show to some extend haemostatic properties. This feature may contribute to stop bleeding which often can not be prevented when preparing the tooth or tooth stump. The astringents can be incorporated into the formulation, if desired. The addition of haemostatic agents sometimes supports the retraction procedure.

The alginate containing composition of the invention typically shows features known from alginate wound dressings known in the art. Alginates which can be used are typically non-toxic, non-sensitising and non-allergenic materials, which have good absorption characteristics by the living body. This may be beneficial should residues of the composition (cured or not cured) remain in the sulcus. Alginates are sometimes said to be biocompatible, meaning that it does not produce a toxic, injurious, or immunological response in living tissue, and/or biodegradable, meaning that residues of the material can be absorbed or degraded by the living body.

Depending on the formulation chosen, the curable retraction composition according to the invention may fulfil at least one of the following features:
a) The composition is biocompatible, b) the composition can be provided in a high viscous (paste-like) form, c) the composition typically might also have a low filler content, d) the cured composition has a sufficient tensile strength, e) setting of the paste may be accomplished at any time by the application of a crosslinker, f) the composition may have inherent or intrinsic haemostatic properties, at least to some extend.

Thus, depending on the formulation chosen a dental composition with improved properties can be provided.

In the context of the present invention, a "composition" is understood to be a mixture of two or more components.

A "curable composition" within the meaning of the invention is a composition which can be hardened within a reasonable time (e.g. within a couple of minutes or seconds, e.g. up to about 10 min or up to about 5 min or up to about 1 min or up to about 30 s or even up to about 5 s) as soon as the curing process has been started, e.g. by applying a curing or setting agent like a crosslinker. Setting can typically be achieved at ambient conditions, (e.g. about 20 to about 40° C.) without applying external heat.

The terms "crosslinking", "hardening", "setting", "curing" or "curable" are used interchangeable, all referring to the formation of material with a higher molecular weight and/or to the formation of a material having a higher viscosity, by creating a network due to chemical and/or physical interaction.

A "hardening, curing or setting reaction" within the meaning of the invention is a reaction wherein physical properties such as viscosity, and tensile strength of a composition change over the time due to a chemical or physical reaction between the individual components.

An "alginate" within the meaning of the invention is a salt of an alginic acid. Alginates are used for making dental impressions since many years. Alginates are usually delivered as powders and form an irreversible hydrocolloide in the presence of water. The alginic acid is a bio-copolymer containing dehydro-D-mannuronic acid and dehydro-L-guluronic acid. A comprehensive review on alginates which can be used in the dental field can be found in: Handbook of Hydrocolloids, Edited by: Phillips, G. O.; Williams, P. A., © 2000 Woodhead Publishing, Chapter 22. Alginate containing materials are sometimes preferred as these materials are biodegradable and thus lower the risk of infection during and after the treatment should material remain in the sulcus. Alginate pastes typically show good flow properties into the sulcus (due to the hydrophilic nature of the material).

The composition of the invention differs from alginate compositions used for making impressions in various aspects.

Alginate compositions used for making impressions are typically provided as powders to be mixed with water before use to obtain a paste. They typically contain a high amount of water (e.g. above about 60 wt.-% with respect to the whole composition) and a high amount of filler (e.g. above about 60 wt.-% with respect to the dry powder). The paste typically cures within a few minutes (e.g. about 2 to about 5 min setting time in the mouth). The tensile strength of the cured impression composition does typically not exceed a value of about 0.7 MPa.

In contrast to this, the mechanical properties of the inventive retraction composition are better, e.g. with respect to tensile strength and/or elongation at break. Moreover, in certain embodiments the inventive composition contains less filler and less solvent.

A "poly-, di- or trivalent ion source" within the meaning of the invention is a component or composition which is able to provide ions with the respective charge, if dissolved in a liquid such as water. That is, the divalent ion source is able to dissociate into cations having a charge of plus at least two (2+) or at least plus tri (3+) and anions to a certain amount over the time.

An "agent being able to retard the setting" within the meaning of the invention is a substance or composition which influences the availability of the cations needed for the curing reaction. They may undergo a chemical reaction with the cations delivered by the di- or trivalent ion source to control the amount of free cations capable to react with the alginate. They also may alter the solubility of the di- or trivalent ion source which is important to control the concentration of the di- or trivalent ions that are capable to react with the alginate. The agents can be of predominantly organic or inorganic nature.

If not otherwise indicated "molecular weight" within the meaning of the invention always means Mw (weight average of the molecular weight) and can be determined for the individual classes of polymers by gel permeation chromatography (GPC) against a standard of defined molecular weight. Suitable measurement methods are known to the person skilled in the art.

The molecular weight of alginates is usually determined by measurement of the viscosity of a defined solution with respect to a calibration curve. The molecular weight of alginates referred to in the invention is based on the information provided by the suppliers.

"Network builders" within the meaning of the invention are components which are able to form a network by a crosslinking reaction between the respective components. This network can be an interpenetrating network, that is a network that interferes with the alginate network or it can be a network that exists besides the alginate network without interference.

A "tooth structure" within the meaning of the invention is any tooth structure, prepared or ready for preparation by the dentist. It can be a single tooth or two or more teeth. A tooth structure is also referred to as hard dental tissue in contrast to soft dental tissue (e.g. gingival).

A "haemostatic agent" within the meaning of the invention is an agent which is able to reduce bleeding to a certain amount and/or causes blood to coagulate.

A "dental composition" within the meaning of the invention is any composition which can be used in the dental field. In this respect the composition should be not detrimental to the patient's health and thus free of hazardous and toxic components being able to migrate out of the composition.

A "dental impression material" within the meaning of the invention is a material used for making impressions of the tooth structure including the gingiva. A dental impression material is usually applied on a dental impression tray. A dental impression material can be based on different chemical substances and crosslink by various chemical reactions (including addition curing and condensation curing materials). Typical examples include silicone based impression materials (e.g. VPS materials) and polyether based impression materials and mixtures of those.

The term "essentially does not" within the meaning of the invention is to be understood that a certain—sometimes unavoidable—effect does usually not take place or only occurs to a minimum amount, wherein the effect does not negatively affect the overall result to be achieved.

The setting behaviour of a curable composition is "not negatively affected" within the meaning of the invention, if the setting of the curable composition takes place within the given specification. Small deviations (e.g. within a range of about 5 to 10%) from given physical parameters like viscosity, working time or setting time, which might occur if e.g. an additive is added or setting takes place in conjunction with other materials or substances (e.g. in the presence of a retraction device), are not considered detrimental.

"Ambient conditions" within the meaning of the invention mean the conditions which the inventive composition is usually subjected to during storage and/or handling. Ambient conditions may, for example, be a pressure of about 900 to about 1100 mbar, a temperature of about −10 to about 60° C. and a relative humidity of about 10 to about 100%. In the laboratory ambient conditions are typically adjusted to about 23° C. and about 1013 mbar.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

DETAILED DESCRIPTION OF THE INVENTION

Figure 1:
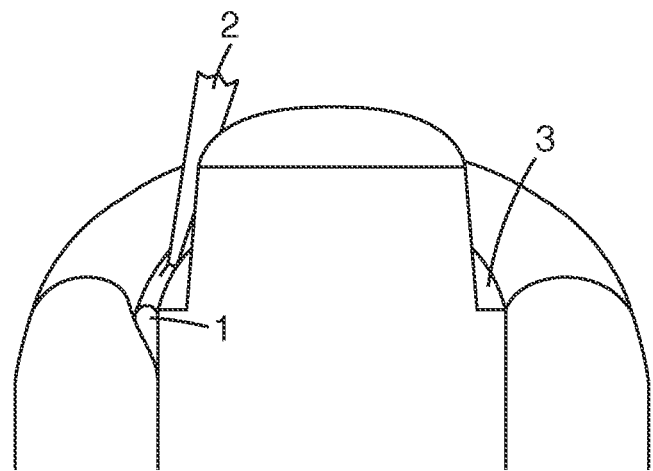
FIGS. 1, 2, 3 and 4 show an embodiment how the curable composition according to the invention can be used.

The curable dental retraction composition comprises an alginate.

The chemical nature of the alginate is not particularly limited, however, the alginates which can be used are usually bio-copolymers containing dehydro-D-mannuronic acid and dehydro-L-guluronic acid. Naturally available hydrogel based materials are preferred. Suitable alginates are alginates from algae. Preferred are alginates from algae *Laminaria hyperborea*. Especially useful are alginates from *Laminaria hyperborea* Steam and from *Lessonia trabeculata*. Also synthetic alginates having a high guluronate content can be used. Preferred salts of these alginic acids are sodium and potassium salts. Especially preferred is the potassium salt.

A particularly preferred class of alginates found to be useful for the present invention has a comparable high guluronate content (e.g. content of guluronate units above about 50 wt.-%). It was found that alginates with a high content of guluronan units can form stronger gels than those with a low guluronan content. Composition which allow the formation of strong gels (e.g. gels with a high tensile strength), can be advantageous for producing compositions to be used for dental retraction.

The guluronate content of alginates which can be used can be above about 30 wt.-% or above about 50 wt.-% or above about 60 wt.-% with respect to the weight of the alginate in dry form. The guluronate content of the alginate can be as high as about 80 wt.-% or about 75 wt.-% with respect to the weight of the alginate in dry form. Ranges which have been found to be useful are about 50 to about 80 wt.-% or between about 60 to about 75 wt.-% with respect to the weight of the alginate in dry form.

The molecular weight (Mw) of the alginate is not particularly limited, either, but typically is in a range between about 200,000 and about 400,000 g/mol or between about 250,000 and about 350,000 g/mol or between about 200,000 and about 300,000 g/mol.

The alginate can have a low particle size. An average particle size up to about 75 μm (d90/μm—that is, in 90% of the analyzed volume, the particles have a size below 75 μm) or up to about 200 μm was found to be useful. The particle size can determined as outlined below.

The particle size can be measured using a Malvern Mastersizer 2000 (Malvern Instruments, Malvern, Worcestershire, UK) light scattering instrument. The Mastersizer 2000 uses an integrated optical system to cover the range from 0.02 to 2000 μm. The mixtures to be analyzed are added to the test chamber filled with iso-propanol until an obscuration of approximately 8-15% is reached. No ultrasound is applied in order not to alter the particle size distributions. The raw data is processed with the instrument software using a refractive index of 1.459 and applying the Mie correction together with the Fraunhofer approximation, frequently used techniques known to the expert.

In one embodiment, the alginate can be present in the curable paste-like composition in an amount of at least about 4 or of at least about 6 or of at least about 10 wt.-% with respect to the whole curable composition. The alginate can be present in the curable composition up to an amount of about 15 or up to about 20 or up to about 30 wt.-% with respect to the whole composition. Thus, useful ranges for the alginate to be used include from about 4 wt.-% to about 30 wt.-% or from about 10 wt.-% to about 20 wt.-% or from about 20 wt.-% to about 30 wt.-%.

The curable dental retraction composition comprises solvent.

Solvents suitable for preparing the dental retraction composition of the invention are those, which are able to form a paste or gel with the alginate.

Typically, the solvent contains a high amount of water (e.g. above about 50 or 70 or 90 vol.-%) or consists of water only. Mixtures with alcohols (e.g. ethanol) or ketons (e.g. acetone) can be used as well. The solvent should essentially be free of di- or trivalent ion sources.

The curable composition of the invention comprises the solvent in an amount sufficient to form a high viscous gel with the alginate. In one embodiment, the dental retraction composition contains the solvent in an amount of at least about 40 wt.-% or at least about 60 wt.-% or at least about 80 wt.-% with respect to the whole curable composition.

Typically the amount of solvent present in the composition does not exceed about 85 wt.-% or about 60 wt.-% or about 40 wt.-% with respect to the whole curable composition.

In another embodiment the curable composition may contain a filler or a mixture of fillers.

The nature of the filler of the inventive composition is not particularly limited. Anorganic or organic fillers or mixture of both can be used, if desired.

A wide variety of inorganic, especially hydrophobic fillers may be employed such as silica, alumina, magnesia, titania, inorganic salts, metallic oxides and glasses. It has been found to be possible to employ mixtures of silicone dioxides, including those derived form crystalline silicon dioxide, such as pulverized quartz; amorphous silicone dioxides, such as a diatomaceous earth and silanated fumed silica, such as Cab-o-Sil TS-530 (160-240 $m^2/g$), manufactured by Cabot Corporation. Varying the sizes and surface areas of the foregoing materials enables one of the cured compositions. Some or all of the foregoing hydrophobic fillers may be surface treated with one or more silanating agents, as known to those of ordinary skill in the art. Such a silanation may be accomplished, e.g., using known halogenated silanes or silazides. Some useful functionalized silicas are commercially available, e.g., products sold under the brands Aerosil™ (Degussa) or HDKH™ (Wacker).

Examples of typical fillers which can be used are non-reinforcing fillers including quartz, cristobalite, calcium silicate, diatomaceous earth, zirconium silicate, wollastonite (e.g. Tremin™), montmorillonite such as bentonite, zeolite, including molecular sieves such as sodium aluminium silicate, metal oxide powder such as aluminium, titanium or zinc oxide or their mixed oxides, barium sulphate, calcium carbonate, plaster, glass and plastic powder. The fillers can be surface treated. The surface treatment can generally be carried out with the same methods as described for reinforcing fillers.

Suitable fillers also include reinforcing fillers such as e.g. pyrogenic or precipitated silicic acid and silica aluminium mixed oxides. The above mentioned fillers can be hydrophobized as well e.g. by treatment with organosilanes or slloxanes or by the etherification of hydroxyl groups to alkoxy groups. One type of filler or also a mixture of at least two fillers can be used.

Useful organic fillers include thermoplastic or elastomeric homo- or copolymer particles, e.g. PP (polypropylene), PE (polyethylene), PTFE (polytetrafluoroethylene), PET (polyethylene terephthalate), PA (polyamide), PEEK (polyetheretherketone), PAI (polyamidimide), PI (polyimide), PPS (polyphenylenesulfide), blends thereof, cellulose powders or organic nanofillers like trimethylsilylglucose, cottonweed, carbon black The structure of the anorganic and organic materials can be of all shape, including solid or hollow fibres of variable length.

The size of the filler particles should be such that a homogeneous mixture with the alginate can be obtained.

Typically, the size of the filler particles is in a range of about 20 nm to about 200 μm, or in a range of about 50 nm to about 150 μm or in a range of about 100 nm to about 100 μm.

If a filler is present, it is typically present in an amount of less than about 60 wt.-% or less than about 50 wt.-% or less than about 40 wt.-%. The filler can be present in an amount of 1 to about 60 wt.-% or in an amount of about 5 to about 50 wt.-% or in an amount of about 15 to about 40 wt.-%.

The curable dental retraction composition may also comprise one or more additives selected from network builder, colourants, haemostatic agents, anti-microbial agents, anti-evaporation agents, flavouring agents, viscosity modifiers, preserving agents, surfactants and mixtures thereof.

These additives can be present in an amount of at least about 0.01 wt.-% or at least about 1 wt.-% with respect to the whole composition.

The additives can be present in an amount up to about 50 wt.-% or at least up to about 20 wt.-% or at least up to about 15 wt.-% with respect to the whole composition.

Typically, those agents or additives can be present in an amount of about 0.01 wt.-% to about 25 wt.-% or of about 0.01 wt.-% to about 20 wt.-% or about 0.1 wt.-% to about 15 wt.-% with respect to the whole composition.

In one embodiment the composition might contain as an additive a network builder to enhance mechanical strength, if needed. The additional network(s) may be build by tailor-made organic or other natural compound(s) like polyether(s), polyvinyl alcohol derivative(s), polyrotaxane(s), cellulose derivative(s), chitosane derivative(s), cyclodextrine(s), derivatives from hyaluronic acid, polyacrylamide(s) or polymethylacrylamide(s), compounds containing reactive (e.g. polymerizable) residues A network builder might not be present at all, but can be present in an amount up to about 25 wt.-% or up to about 50 wt.-% with respect to the whole composition. If a network builder is present, it is typically present in an amount of at least about 3 wt.-% or at least about 10 wt.-% with respect to the whole curable composition.

The curable composition may also contain an agent being able to retard the setting of the curable dental retraction composition (retarder), if desired. The manner how the availability of cations (2+ and/or 3+) that are able to react or interact with the alginate is controlled may have an influence on the curing speed, the gelation kinetics and/or on physical properties of the cured composition like tensile strength or elongation at break.

In a couple of embodiments of the invention, no retarder is present at all, especially in those embodiments where the curing or hardening reaction should not be delayed. However, in other embodiments of the invention a delay of the hardening reaction might be desired.

Typical retarders include inorganic phosphates and organic acids like citric acid or EDTA. Substances, which are able to retard the setting reaction are typically water-soluble. The organic acids may be present as salts. The inorganic phosphates and the salts of the organic acids usually have alkali (e.g. Li, Na, K) and ammonium cations as counter ions.

In a preferred embodiment, the agent being able to retard the setting can undergo a change in the chemical structure such as a ring-opening of a cyclic structure in an acidic environment. Agents with a cyclic structure may contain ester or urethane units. The ring itself is usually comprised of five or six atoms such as carbon, oxygen or nitrogen atoms.

If a retarder is present, the amount of the agent being able to retard the setting is not particularly limited as long as the intended needs in the dental field can be met. Typically the agent is used in an amount of at least about 1 wt.-% or of at least about 5 wt.-% or of at least about 15 wt.-%. The agent can be used up to an amount of about 50 wt.-% or up to an amount of about 40 wt.-% or up to an amount of 20 wt.-%. Thus, typical ranges for the amount of the above mentioned agent are from about 0.1 to about 50 wt.-%, or from about 0.5 to about 40 or from about 1 to about 30 wt.-% with respect to the whole curable composition.

In a further embodiment, the dental retraction composition has a colour which may allow an easy detection in a patient's mouth (especially compared to oral tissue and/or tooth substance) and control whether after the treatment all residues of the retraction device have been removed from the sulcus. E.g., a blue, green or violet colour may be suitable. However, in view of some new impression techniques like e.g. digital scanning, other colours might be preferred. Some techniques prefer colours that are less visible for the scanning instrument e.g. red or white. Colouring of the retraction device can be achieved by incorporating colorants or pigments (organic and inorganic) into the composition.

Examples of colourants which can be used include red iron oxide 3395, Bayferrox 920 Z Yellow, Neazopon Blue 807 (copper phthalocyanine-based dye) or Helio Fast Yellow ER.

In a further embodiment the dental retraction composition may comprise one or more haemostatic agents. Haemostatic agents (sometimes also referred to as astringent agents) that may be useful in assisting haemostasis include, but are not limited to oxides, chloride or sulphate salts of ferrum (e.g. ferric sulfate, ferric subsulfate, ferric chloride), aluminium (e.g. potassium aluminum sulfate, aluminum ammonium sulfate, aluminum sulfate, aluminum chlorohydrate, aluminum acetate) and zinc, polyphenols, ellag acid, permanganates (e.g. potassium permanganate), silver nitrate and hydrogen peroxide and mixtures thereof. One preferred class of haemostatics include aluminum compounds.

Suitable biopolymers and polysaccharides, which might contribute to an haemostatic effect include cellulose, celluloses derivates, gelatine, starch, starch derivates, collagen, alginate, chitin, chitosan, or hyaloron acid.

Physically effective haemostyptica include phytogenic or mineral zeolites, micro porous polysaccharide spheres, kaolin and celite.

Pharmaceutical drugs which might contribute to a haemostatic effect include adrenaline, epinephrine, propylhexidrin, adrenochrom-monosemicarbazone propylgallat, tranexamic acid, etamsylate, batroxobin, thrombin, fibrin dressings.

If a haemostatic agent is present, it is typically present in an amount of about 0.01 wt.-% to about 25 wt.-% or in an amount of about 0.1 wt.-% to about 15 wt.-% or in an amount of about 0.5 wt.-% to about 5 wt.-% with respect to the whole curable composition.

In another embodiment, the curable composition comprises an anti-microbial agent. This might help reducing health risks for professionals in the dental offices and laboratories as well as for patients caused by bleeding prior impression taking caused by drilling or retracting the gingival cuff. It may reduce the risk of contamination of the patient having a wound as well as the risk of contamination of the impression taken, thus preventing contamination of dental professionals in the dental office as well as of the dental lab.

To provide an efficient and time-saving solution the curable composition can contain the anti-microbial component when delivered to the dentist. The composition can also contain an astringent agent in addition.

It can be beneficial, if residues of the retraction device which were left in the sulcus by accident do not interfere with or negatively affect the setting reaction of the impression material used after the retraction procedure.

It is known that some haemostatics which are used in solution or together with retraction cords (the cord may be impregnated or soaked in the solution prior use) can compromise the setting reaction of certain impression materials.

For instance, as indicated in the instruction of use of certain impression materials, epinephrine (adrenaline), 8-hydroxyquinoline sulfate or iron (III) sulfate may impair the setting behaviour.

Therefore, it can be an advantage, if the anti-microbial agent used is compatible with the impression material to be used and does not compromise the setting behaviour thereof.

Furthermore, it can be advantageous to use combinations of anti-microbial compounds to generate an additive or synergistic effect.

Useful combinations include chlorhexidine or derivatives thereof and aldehydes (glutaraldyde, phtaldehyde) and chlorhexidine or its derivatives and salts of phenolics or acids. It can also be preferred to use acid adducts of chlorhexidine or its derivatives like e.g., acetates, chlorides, nitrates, sulfates or carbonates.

Chlorhexidine and its derivatives (hereinafter referred to as CHX) are commercially available in water-based solutions (e.g. a 20% aqueous solution of CHX digluconate, CAS 18472-51-0) or as a pure compound or as a salt. As additive to non-water based impression materials the pure compound (CAS 55-56-1) and CHX salts like CHX diacatate monohydrate (CAS 56-95-1) or CHX dihydrochloride (CAS 3697-42-5) are preferred.

CHX also seems to be especially suited as an additive due in part to its well-known and proven anti-microbial action against Gram positive and Gram negative microorganisms including the oral Streptococci and Lactobacilli. CHX is bacteriostatic for Mycobaterium. CHX is also active against yeasts including Candida albicans and viruses including HIV, HBV, HCV, Influenza- and Herpes virus. A further advantage of CHX is its low toxicity.

Preferred anti-microbial agents include: Hexitidin, Cetypyridiniumcloride (CPC), Chlorhexidin (CHX), Triclosan, Stannous Chloride, Benzalkonium Chloride, non-ionic or ionic surfactants (e.g. quarternary ammonium compounds), alcohols [monomeric, polymeric, mono-alcohols, poly-alcohols (e.g. Xylitol, Sorbitol), aromatic (e.g. phenol)], antimicrobial peptides (e.g. histatins), bactericins (e.g. nisin), antibiotics (e.g. tetracycline), aldehydes (e.g. glutaraldehyde) inorganic and organic acids (e.g. bencoic acid, salicylic acid, fatty acids) or there salts, derivative of such acids such as esters (e.g. p-hydroxy benzoate or other parabenes, lauricidin), enzymes (e.g. lysozyme, oxidases), proteins (e.g. enamel matrix protein, prolin rich proteins), fluoride, EDTA, essential oils (e.g. thymol). Several silver containing components are reported to have an antimicrobial effect, too.

An example of a useful combination of an anti-microbial agent and an astringent agent is aluminium chloride or partially neutralized aluminium chloride and CHX dichloride.

If an anti-microbial agent is present, it is typically present in an amount of about 0.01 wt.-% to about 5 wt.-% or in an amount of about 0.1 wt.-% to about 1 wt.-% with respect to the whole curable composition.

In another embodiment a vasoconstrictor such as epinephrine and/or propylhexedrine can be added.

The curable dental retraction composition may also comprise an anti-evaporating agent including glycerine or polyethylene glycols (e.g. having a molecular weight Mw in the range of about 200 g/mol to about 10,000 g/mol or in a range of about 500 g/mol to about 3,000 g/mol). If an anti-evaporating agent is present, it is typically present in an amount of about 0.01 wt.-% to about 40 wt.-% or in an amount of about 1 wt.-% to about 10 wt.-% with respect to the whole curable composition.

In another embodiment, the curable dental retraction composition may comprise one or more viscosity modifiers. Materials which may provide a viscosity modifying effect include fibrillated fibres (as suggested in US 2005/0287494) e.g. natural fibres based on cellulose or man-made fibres e.g. polyester, polyamide or fibres of glass. Starch and silicone oil can also be used as viscosity modifiers (cf. WO 2006/057535) alone or in addition to fibrillated fibres.

There is no need for a viscosity modifier to be present at all. However, if it is present, it is typically present in an amount of up to about 0.01 wt.-% or up to about 1 wt.-% or up to about 20 wt.-%, with respect to the whole curable composition.

In another embodiment, the curable dental retraction composition may comprise one or more surfactants. Typical surfactants, which can be used, include anionic, cationic or non-ionic surfactants.

There is no need for a surfactant to be present at all. However, if it is present, it is typically present in an amount of up to about 0.01 wt.-% or up to about 1 wt.-% of up to about 2 wt.-%, with respect to the whole curable composition.

In a specific embodiment, the inventive curable dental retraction composition comprises
- the alginate in an amount of about 5 wt.-% to about 40 wt.-% or of about 10 wt.-% to about 30 wt.-% or of about 12 wt.-% to about 20 wt.-%,
- the solvent in an amount of about 20 wt.-% to about 90 wt.-% or of about 30 wt.-% to about 80 wt.-% or of about 40 wt.-% to about 70 wt.-%,
- the filler in an amount of about 0 wt.-% to about 80 wt.-% or of about 7 wt.-% to about 60 wt.-% or of about 10 wt.-% to about 40 wt.-% and
- additives in an amount of about 0 wt.-% to about 50 wt.-% or of about 0.5 wt.-% to about 30 wt.-% or of about 1 wt.-% to about 15 wt.-%; wt.-% with respect to the whole composition.

According to a preferred embodiment, the curable dental retraction composition of the invention (before the application of a crosslinker or crosslinker composition) has a viscosity of at least about 40 kPa*s or at least about or at least about 60 kPa*s or at least about 80 kPa*s measured with a shear rate of 0.2 $s^{-1}$ (23° C.).

There is no fixed upper limit, however, the viscosity of the curable composition typically does not exceed values above about 700 kPa*s or above about 300 kPa*s or above about 250 kPa*s measured with a shear rate of 0.2 s$^{-1}$ (23° C.).

The curable composition of the invention is preferably provided to the practitioner under hygienic conditions. One possibility to achieve this is packing the retraction device in a sealed container such as a capsule or cartridge or foil bag under hygienic conditions.

Thus, the inventive curable dental retraction composition is typically stored in a container. Usually the container has a front end and a rear end, a piston movable in the container and a nozzle for delivering or dispensing the composition located in the container. The container has usually only one compartment.

The composition can be dispensed out of the container by moving the piston in the direction of the nozzle. The piston can be moved either manually or with the aid of an application device designed to receive the container (e.g. an application device having the design of a caulk gun).

Examples of containers which can be used include compules, syringes and screw tubes. Typical containers of this kind are described in more detail e.g. in U.S. Pat. No. 5,927,562, U.S. Pat. No. 5,893,714 or U.S. Pat. No. 5,865,803, the content of which in regard to the description of containers is herewith incorporated by reference.

The invention also features a kit of parts, comprising at least 2 parts, one of which comprises the curable dental retraction composition and one of which comprises a crosslinker or crosslinker composition. These parts are typically separated from each other during storage to avoid an unwanted prematurely curing of the curable dental retraction composition.

The crosslinker is not part of the inventive curable dental retraction composition from the very beginning. The crosslinker is added to the composition or applied at least to the surface of the composition in a separate step. Upon addition or application of the crosslinker to the curable composition or to at least a part of the surface thereof, the setting process of the curable composition is started.

Typically, the crosslinker is selected from di- or trivalent ion sources. The nature of the poly- di- or trivalent ion source is not particularly limited. In principle any di- or trivalent ion source can be used being able to form a temporary or permanent complex with the alginate. Ions forming irreversible complexes with the alginates are preferred. Ions which can be used include ions selected from Ca, Ba, Zn, Co, Mn, Cu, Al, Zr, Ti, Si, Ag and Fe or mixtures thereof.

The nature of the counter ion is not particularly limited, either. Counter ions found to be useful are phosphate, hydrogenphosphate, sulfate, carbonate, fluoride, chloride, bromide, oxalate, acetate, succinate, citrate, or ascorbate. The di- or trivalent ion source may contain in addition crystal water.

From the divalent ions calcium is often preferred. A preferred source of calcium ions are good soluable calcium salts like calcium sulfate, calcium carbonate, calcium chloride, calcium oxalate or calcium ascorbate or complexes of calcium with EDTA. Barium carbonate, copper(II) carbonate in which crystal water might be incorporated are also useful divalent ion sources.

The crosslinker is typically dissolved in a solvent like water, alcohol (e.g. ethanol, iso-propanol) or mixtures of water and alcohol(s). Crosslinker and solvent are then parts of a crosslinker composition.

The solution containing the crosslinker can comprise other additives as well. Principally, all additives which might be present in the curable dental retraction composition described in the text of the present invention can also be present in the solution containing the crosslinker.

Such additives include network builder, colorants, haemostatic agents, anti-microbial agents, anti-evaporation agents, flavouring agents, viscosity modifiers, preserving agents, polymers, and mixtures thereof.

Thus, in certain embodiments the additives described in the text of the invention can be present only in the curable retraction composition, or only in the crosslinker composition or in both compositions, the curable retraction composition and the crosslinker composition. It is also possible that only a few additives are present in the curable retraction composition and other additives are present in the crosslinker composition.

The poly-, di- or trivalent ion source (including crystal water if present) can be present in the crosslinker composition in an amount of at least about 5 or at least about 8 or of at least about 12 or of at least about 15 wt.-% with respect to the crosslinker composition. The divalent ion source can be present in the crosslinker composition in an amount up to about 10 or up to about 40 up to about 70 wt.-% with respect to the crosslinker composition. Ranges which have been found to be useful are from about 5 to about 40 or from about 8 to about 50 or from about 12 to about 40 wt.-% with respect to the crosslinker composition.

If the crosslinker is dissolved in a solvent forming a crosslinker composition, the viscosity of the crosslinker composition should be such that an easy application is possible. Typically, the crosslinker composition is in liquid form at ambient conditions in order to achieve sufficient wetting of and/or penetration into the curable dental retraction composition.

Good results can be obtained with a solution having a dynamic viscosity of about 1.0 mPa*s up to about 100 mPa*s or up to about 80 mPa*s or up to about 60 mPa*s at 23° C.

The dynamic viscosity can be determined with an Physica MCR301 instrument using a cone plate geometry, diameter 50 mm, angle (cone) 1°, at 23° C. A typical shear rate is 200 rounds/s, however, generally the viscosity of liquids is independent from the shear rate in a wide range.

The crosslinker or crosslinker composition is typically stored in separate device such as a bottle or flask having an opening with nozzle. In another embodiment, the bottle or flask contains an atomizer, that is, it is equipped with a device which allows transforming a liquid into tiny particles.

The invention is also related to a process of crosslinking the inventive curable dental retraction composition, wherein the process comprises the steps of
providing the curable dental retraction composition and the crosslinker or crosslinker composition described in the text of the present invention,
bringing into contact the curable dental retraction composition and the crosslinker or crosslinker composition.

The term "bringing into contact" means that the crosslinker is at least applied to at least a part of the surface of the curable dental retraction composition or vice a versa. However, it may also be mixed with the curable dental retraction composition if this is feasible. The step of "bringing into contact" can be accomplished e.g. by dipping, spraying or brushing.

The sequence of the application steps is equal and independent from each other and can also be repeated, if desired. Thus, according to one embodiment the curable dental retraction composition is provided or applied first, followed by the application of the crosslinker or crosslinker composition.

According to another embodiment of the invention, the crosslinker or crosslinker composition is provided or applied first, followed by the application of the curable dental retraction composition. In yet another embodiment, the crosslinker or crosslinker composition is provided or applied first. In an additional step the curable dental retraction composition is provided or applied. In a further additional step, the crosslinker or crosslinker composition is provided or applied again.

It is also possible that between these steps one or more intermediate steps take place including a rinsing or cleaning step.

The invention is also directed to a cured dental retraction composition obtainable according to the process described in this text.

If the crosslinker is applied only to the surface of the curable dental retraction composition, the hardening process starts in this region and may continue until the whole composition is set. This process might be controlled by a diffusion process of the crosslinker components into and through the dental retraction composition. Thus, at the surface of the dental retraction composition the setting reaction might already be finished whereas in other parts of the setting reaction the setting reaction has not started yet. Typically, the setting reaction does not proceed homogeneously having the effect that the cured dental retraction composition can be divided into different portions ranging from completely set portions to uncured portions. According to one embodiment, the crosslinker or crosslinker composition is applied plentifully around the preparation (that is, the region to be treated) causing the curable dental retraction composition to harden rapidly and more or less completely.

In the case were uncured residues of the dental retraction composition remain in the sulcus and cannot easily be removed, e.g. if the sulcus is deep and/or tight, the remaining uncured residues can be post-hardened by applying or bringing into contact these residues with the crosslinker or crosslinker composition in an additional step, especially in this localized area.

Upon application of the crosslinker or crosslinker composition to at least a part of the surface of the curable dental retraction composition, the latter one begins to set resulting in a high viscous gel which usually does not show a flowing behaviour anymore under the conditions in the patient's mouth.

The setting or curing reaction can typically be accomplished within a short period of time. Typically, the setting reaction is completed within about 5 min or within about 1 min or within about 5 s. The term "completed" within this context means that the composition does not undergo alterations with regard to viscosity visible to the human eye.

In one embodiment the cured composition shows a tensile strength of at least about 0.4 MPa or of at least about 0.5 MPa or of at least about 0.6 MPa measured according to "Measurement of tensile strength and elongation at break" given in the experimental section.

In another embodiment the cured composition shows an elongation at break value of at least about 15% or of at least about 40% or of at least about 50% measured according to "Measurement of tensile strength and elongation at break" given in the experimental section.

The kit of parts described in the present invention may also comprise besides a curable retraction composition as defined in the present text and a crosslinker or crosslinker composition as a further part a curable impression material, the setting behaviour of which is not negatively affected if cured in the presence of the retraction device.

The impression materials which can be used in combination with retraction devices are not particularly limited in regard to their chemistry and nature. Polyether moieties or silicone moieties containing impression materials have found to be useful. In a preferred embodiment, the cured composition becomes part of the impression material to be applied after the retraction procedure. This saves time for the dentist as there is no need to remove the cured paste from the sulcus anymore.

Examples of polyether moieties containing impression materials are given in U.S. Pat. No. 6,383,279, US 2002/0156149 and US 2005/0250871. Commercially available materials are sold e.g. under the brand Impregum™ (3M ESPE).

The kit may further comprise accessories like retraction caps. Retraction caps can be useful for keeping the retraction material in place until an impression is taken or pushing the curable or cured dental retraction composition into the sulcus. Retraction caps can be made of soft, tissue friendly material, e.g. cotton. However, other materials might be useful as well. If appropriate a temporary restoration can be used as retraction cap, too. Commercially available retraction caps are e.g. sold under the brand Comprecap™ (Coltène Whaledent).

In a further embodiment, the invention relates to a method of using an alginate for retraction of soft dental tissue (e.g. gingival) away from hard dental tissue (e.g. tooth) before taking an impression, wherein the alginate is essentially free of a crosslinker component.

Typically, the above method comprises the steps of applying or packing the curable dental retraction composition into the sulcus between soft and hard dental tissue. In some cases compression caps or bridges, temporary crowns or bridges or even a first impression might be used as a kind of accessory during the retraction process. Typically, the curable composition remains in the sulcus for a couple of minutes (e.g. about 1 to about 10 or about 2 to about 6 min to achieve effective mechanical retraction.

The application of the crosslinker or crosslinker composition can be done at any time, the dental practitioner deems useful. Typically, the crosslinker is applied before an impression of the soft and/or hard dental tissue is done.

For a certain embodiment the application procedure is exemplified in FIGS. 1 to 4.

FIG. 1: After mixing the components, the curable dental retraction composition (1) is dispensed by means of an applier out of a nozzle (2) of a capsule (not shown) into the sulcus (3) of a tooth structure.

Figure 2:
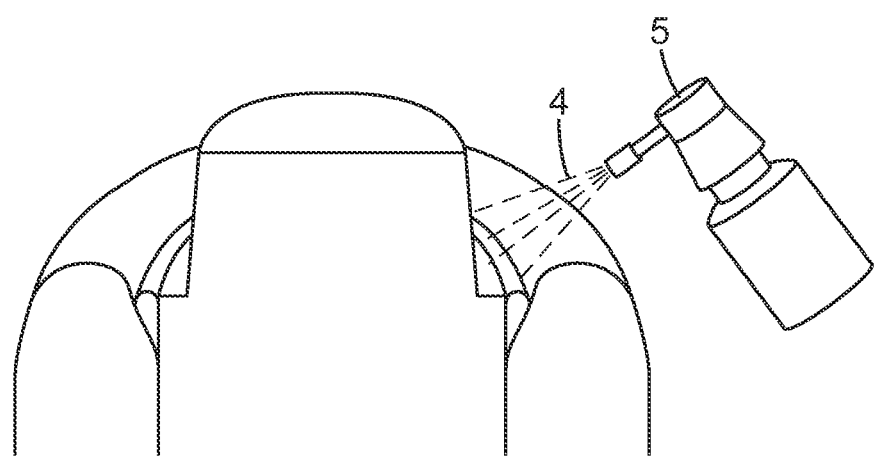

FIG. 2: After an appropriate time period, a crosslinker composition (4) stored in a container (5) with an atomizer is applied to the visible surface of the retraction composition. The curing process typically starts immediately resulting in a cured product. After curing, the cured composition may be pushed deeper into the sulcus with the aid of a dental instrument, if desired (not shown).

Figure 3:
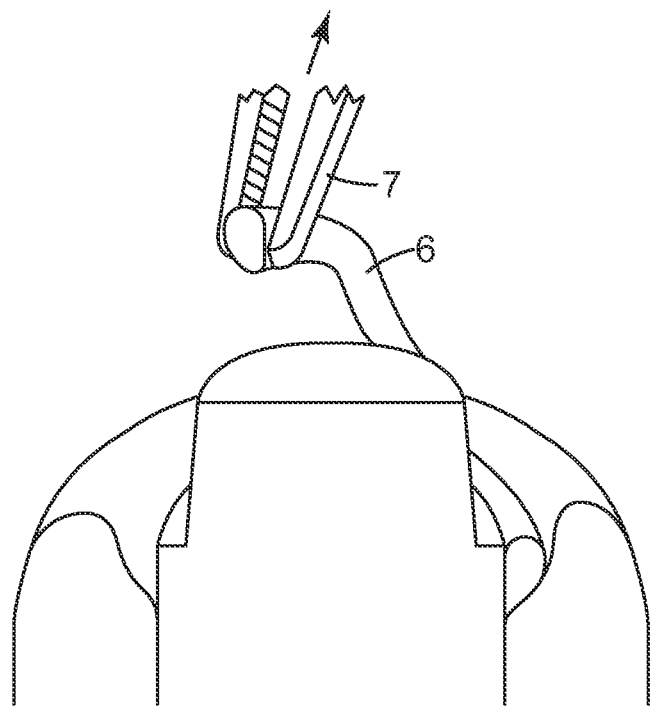

FIG. 3: After sufficient retraction, the cured composition (6) can be removed from the sulcus like a cord using an application instrument (7) such as a pincer.

Figure 4:
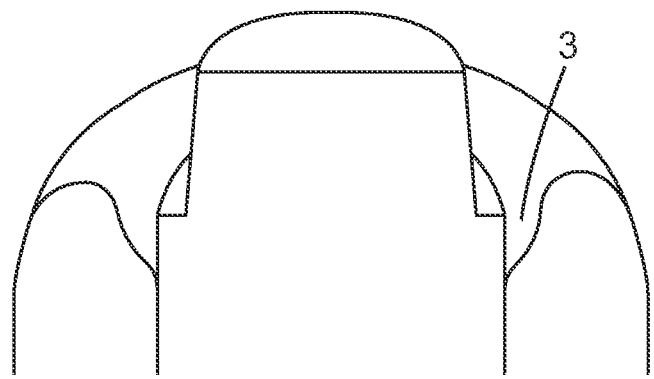

FIG. 4: The sulcus (3) has been widened due to the application of the inventive retraction composition compared to the sulcus before the application. After removal of the cured composition an impression-taking process with a common impression material can follow (not shown).

Typically, the curable composition can be fast and easily applied to the sulcus and removed after curing therefrom, preferably in one piece. Due to biocompatible and non sticky surface properties of the alginate containing composition, the composition can usually be removed without damaging the sulcus.

The following examples are given to illustrate, but not limit, the scope of this invention. Unless otherwise indicated, all parts and percentages are by weight.

EXAMPLES

If not reported otherwise, all tests were conducted at ambient conditions (23° C.; 50% humidity and room pressure). The following substances were used (Table 1):

Measurements
Viscosity

The viscosity was evaluated using a rheometer MCR 300 manufactured by Anton Paar equipped with a 8 mm parallel plate geometry with flat surfaces. The tests were performed at 23° C. The temperature was controlled within 0.1° C. by a Peltier element in the lower plate. The measurement gap was constant at 0.2 mm.

The measurement was performed at a permanent increasing medial shear rate between 0 and 2 s$^{-1}$. The rheometer recorded one data point per 0.1 s$^{-1}$ step and each measurement point lasted for 10 seconds. In the table below, the value for a shear rate of 0.2 s$^{-1}$ is reported.

Tensile Strength and Elongation at Break

The method was done in accordance with ISO 37 with a slightly variance of test specimens.

For testing alginate pastes the thickness of the dumb-bell test piece type 2 was reduced from 2 mm down to 0.5 mm. The measurements were performed with a universal test machine (UPM Z020, Zwick). Before testing, the dies were filled with paste and the surface of the paste moistened with the crosslinker composition (amount of crosslinker used: 0.5 ml crosslinker solution per 0.5 g of retraction composition). The specimens were allowed to cure for 90 s (seconds) at 23° C. and at 50% relative humidity before testing. The test velocity was 200 mm/min and the force sensor was calibrated up to 5 kN. Tensile strength and elongation at break values were determined.

Compositions
Abbreviations

TABLE 1

| Description | Tradename | Availability |
|---|---|---|
| potassium alginate (guluronic content of about 65% and a particle size of about 75 μm) | KF 200 S | FMC Polymer, Norway |
| Quartz flour | Sikron SF 600 | Quarzwerke Frechen GmbH, Germany |
| Quartz flour | Sikron SF 500 | Quarzwerke Frechen GmbH, Germany |
| Quartz flour | Sikron SH 500 | Quarzwerke Frechen GmbH, Germany |
| Chlorhexidine (CHX) | | Aldrich |
| Fumed silica | Aerosil A 380 | Degussa, Germany |
| Bentonite | | Aldrich |
| Kaolin | | Aldrich |
| Tranexamic acid | | Aldrich |
| Aroma | | Vogele, Germany |
| CaCl$_2$ | | |

Synthesis of Curable Paste

The compositions described in Table 2 below were generally prepared as follows:

Component A: Alginate, filler and colouring agent were homogenized by mixing in a speedmixer for 30 s at 2,400 rpm.

Component B: CHX and aroma were dissolved in water.

Component A and B were mixed for 90 s at 2,400 rpm using a speedmixer. The mixing process was started immediately after bringing the components in contact. The mixing step was repeated if the obtained paste was cloddy.

Synthesis of Crosslinker Composition

The crosslinker composition was obtained by dissolving calcium chloride dehydrate in water (10 wt.-% aqueous calcium chloride solution).

Different compositions were prepared and their properties analysed (Table 2)

TABLE 2

| Composition 1 | Percentage [wt.-%] | Viscosity/-Shear rate [Pas]/[1/s] | Tensile Strength [MPa] | Elongation at Break [%] |
|---|---|---|---|---|
| KF 200 S | 16.63 | 69,250/0.2 | 1.77 | 70.6 |
| Aerosil A 380 | 8.31 | (4,738) | (0.29) | (8.9) |
| Sikron SF 600 | 8.31 | | | |
| Water | 66.50 | | | |
| Chlorhexidine | 0.25 | | | |
| 1 drop aroma | | | | |
| Composition 2 | [wt.-%] | [Pas]/[1/s] | [MPa] | [%] |
| KF 200 S | 16.63 | 76,250/0.2 | 1.95 | 69.5 |
| Aerosil A 380 | 8.31 | (6,010) | (0.27) | (11.8) |
| Sikron SF 500 | 8.31 | | | |
| Water | 66.50 | | | |
| Chlorhexidine | 0.25 | | | |
| 1 drop aroma | | | | |
| Composition 3 | [wt.-%] | [Pas]/[1/s] | [MPa] | [%] |
| KF 200 S | 16.63 | 64,150/0.2 | 1.78 | 65.7 |
| Aerosil A 380 | 8.31 | (1,061) | (0.46) | (17.4) |
| Sikron SH 500 | 8.31 | | | |
| Water | 66.50 | | | |
| Chlorhexidine | 0.25 | | | |
| 1 drop aroma | | | | |
| Composition 4 | [wt.-%] | [Pas]/[1/s] | [MPa] | [%] |
| KF 200 S | 18.96 | 101,350/0.2 | 1.73 | 50.0 |
| Aerosil A 380 | 14.21 | (5,162) | (0.35) | (14.9) |
| Water | 66.35 | | | |
| Chlorhexidine | 0.24 | | | |
| heliogenblau | 0.24 | | | |
| 1 drop aroma | | | | |
| Composition 5 | [wt.-%] | [Pas]/[1/s] | [MPa] | [%] |
| KF 200 S | 14.96 | 59,600/0.2 | 1.69 | 90.8 |
| Aerosil A 380 | 7.48 | (8,061) | (0.25) | (16.8) |
| Sikron SH 500 | 7.48 | | | |
| Water | 59.86 | | | |
| Chlorhexidine | 0.22 | | | |
| Tranexamic acid | 10.00 | | | |
| 1 drop aroma | | | | |
| Composition 6 | [wt.-%] | [Pas]/[1/s] | [MPa] | [%] |
| KF 200 S | 16.63 | 61,550/0.2 | 1.64 | 55.3 |
| Aerosil A 380 | 8.31 | (354) | (0.20) | (9.7) |
| Kaolin | 8.31 | | | |
| Water | 66.50 | | | |
| Chlorhexidine | 0.25 | | | |
| 1 drop aroma | | | | |

TABLE 2-continued

| Composition 7 | [wt.-%] | [Pas]/[1/s] | [MPa] | [%] |
|---|---|---|---|---|
| KF 200 S | 16.63 | 72,150/0.2 | 1.73 | 63.1 |
| Aerosil A 380 | 8.31 | (3,889) | (0.25) | (11.4) |
| Bentonite | 8.31 | | | |
| Water | 66.50 | | | |
| Chlorhexidine | 0.25 | | | |
| 1 drop aroma | | | | |

| Composition 8 | [wt.-%] | [Pas]/[1/s] | [MPa] | [%] |
|---|---|---|---|---|
| KF 200 S | 18.13 | 69,600/0.2 | 2.04 | 60.4 |
| Aerosil A 380 | 9.07 | (990) | (0.24) | (11.5) |
| Calciumwolframat | 9.07 | | | |
| Water | 63.46 | | | |
| Chlorhexidine | 0.27 | | | |
| 1 drop aroma | | | | |

| Composition 9 (Reference) | [wt.-%] | [Pas]/[1/s] | | |
|---|---|---|---|---|
| Seaweed meal containing laminaria digitata | 46.1 | 12,300/0.2 (990) | Tensile strength and elongation at break values were not measurable because of the non curing system | |
| deionisized water | 53.9 | | | |

The standard deviation is given in brackets.

Pastes containing alginate, water and filler as described above showed good handling properties like non-sticking behaviour and good pack-ability. A successful retraction of synthetic tissue around a tooth preparation in in-vitro tests using e.g. a Frasaco™ Standard Model AG3 was observed. Moreover, the cured composition could be easily removed e.g. by using a Heinemann spatula.

The invention claimed is:

1. A curable dental retraction composition comprising at least 10 wt % of alginate, from about 5 wt % to about 40 wt % of inorganic filler, and a solvent, with the proviso that essentially no crosslinker in an amount effective to start setting of the curable dental retraction composition is present; wherein the curable dental retraction composition has the consistence of a paste, and the Tensile Strength of the cured dental retraction composition is at least about 0.4 MPa; wherein the curable dental retraction composition does not contain a retarder; and wherein wt.-% is with respect to the weight of the whole composition and wherein the composition has a viscosity of at least 40 kPa*s or higher when measured with a shear rate of $0.2$ $s^{-1}$ (23° C.).

2. The dental retraction composition according to claim 1 comprising at least one additives selected from the group of network builder, colorants, haemostatic agents, anti-microbial agents, anti-evaporation agents, flavouring agents, viscosity modifiers, surfactants preserving agents, polymers, crosslinked systems and mixtures thereof.

3. The dental retraction composition according to claim 2, wherein the components are present in the following amounts:
Alginate: from 10 wt.-% to about 80 wt.-%
Solvent: from about 10 wt-% to about 85 wt.-%
Filler: from about 5 wt-% to about 40 wt.-%
Additives: from 0 to about 75 wt.-%;
wt.-% with respect to the whole composition.

4. The dental retraction composition according to claim 1, wherein the alginate is selected from *Laminaria hyperborea* stem, *Laminaria hyperborean* leaf, *Lessonia trabeculata, Laminaria digitata, Macrocystis pyrifeira, Lessonia nigrescens, Ascophyllum nodosum, Laminaria japonica, Durvillea potatorum, Durvillea antarctica*, bacterial alginate and mixtures thereof.

5. The dental retraction composition according to claim 2, wherein the filler has a particle size in the range of about 20 nm to about 200 μm.

6. The dental retraction composition according claim 1 being contained in a container having a front end and a rear end, a piston movable in the container and a nozzle for delivering the composition located in the container.

7. A kit comprising two parts, the first part comprising the curable dental retraction composition according to claim 1 and a second part, the second part comprising a crosslinker effective to start setting of the dental retraction composition.

8. The kit of claim 7, wherein the crosslinker comprises a di-, tri or polyvalent cation source capable of forming an alginate salt.

9. The kit according to claim 7, wherein the di- or polyvalent cation source is present in the crosslinker in an amount of at least about 0.01 mol/l.

10. A process of curing a curable dental retraction composition, the process comprising the steps of
providing the curable dental retraction composition according to any of claim 1 and the crosslinker as described in claim 8 and
bringing into contact the curable dental retraction composition and the crosslinker; and wherein
the curable dental retraction composition has a viscosity of at least 40 kPa*s or higher when measured with a shear rate of $0.2$ $s^{-1}$ (23° C.).

11. A cured dental retraction composition obtainable according to the process of claim 10, fulfilling at least one of the following features:
Tensile Strength: at least about 0.4 MPa,
Elongation at break: at least about 15%,
measured according to ISO 37 using test specimens having the dimensions of a dumb-bell test piece type 2 with reduced thickness of 0.5 mm, and wherein the curable dental retraction composition has a viscosity of at least 40 kPa*s or higher when measured with a shear rate of $0.2$ $s^{-1}$ (23° C.).

12. A method of using an alginate for the production of a curable retraction composition of claim 1 for retracting soft dental tissue from hard dental tissue, wherein the curable retraction composition is essentially free of a crosslinker component, the method comprising the step of applying the curable dental retraction composition to dental tissue.

13. The method of claim 12, comprising the steps of
dispensing the curable dental retraction composition into the sulcus between soft and hard dental tissue and
applying a crosslinker to at least the visible surface of the dental retraction composition, or
applying a crosslinker into the sulcus between soft and hard dental tissue and
dispensing the curable dental retraction composition into the sulcus between soft and hard dental tissue
wherein the crosslinker is able to start hardening of the curable retraction composition.

14. The dental retraction composition according to claim 1 wherein the composition comprises at least 12 wt.-% of alginate.

15. The dental retraction composition according to claim 1 wherein the alginate has an average particle size of no more than 200 μm.

16. The dental retraction composition according to claim 1, wherein the inorganic filler is hydrophobic.

17. The dental retraction composition according to claim 1, wherein the inorganic filler is selected from the group consisting of silica, magnesia, titania, glass, quartz, calcium silicate, diatomaceous earth, zirconium silicate, wollastonite, montmorillonite, sodium aluminum silicate, aluminum oxide, zinc oxide, barium sulphate, calcium carbonate, plaster silica aluminum mixed oxides or combinations thereof.

18. The dental compositions according to claim 17, wherein the inorganic filler comprises at least one type of silica selected from crystalline silica, amorphous silica, and silanated fumed silica.

19. The kit of claim 7, wherein the second part further comprises a solvent selected from the group consisting of water, ethanol, isopropanol, and mixtures thereof.

20. The kit of claim 7, wherein the crosslinker comprises ionic calcium.

21. The kit of claim 7, wherein the second part comprises at least one additive selected from the group of network builder, colorants, haemostatic agents, anti-microbial agents, anti-evaporation agents, flavouring agents, viscosity modifiers, surfactants preserving agents, polymers, cross-linked systems and mixtures thereof.

22. The kit of claim 7, wherein the retraction composition and the second part are not in contact with one another.

* * * * *